United States Patent [19]

Ogiso

[11] Patent Number: 4,873,081
[45] Date of Patent: Oct. 10, 1989

[54] PERCUTANEOUS ABSORPTION PREPARATION

[75] Inventor: Taro Ogiso, Higashiosaka, Japan

[73] Assignee: Maraho Co., Ltd., Osaka, Japan

[21] Appl. No.: 31,241

[22] Filed: Mar. 26, 1987

[30] Foreign Application Priority Data

May 7, 1986 [JP] Japan .................. 61-105350

[51] Int. Cl.$^4$ ............. A61K 31/40; A61K 31/54; A61K 31/78
[52] U.S. Cl. ............................ 424/81; 514/220; 514/419; 514/420; 514/946; 514/947
[58] Field of Search ............. 514/220, 946, 947, 419, 514/420; 424/81

[56] References Cited

U.S. PATENT DOCUMENTS

| | | | |
|---|---|---|---|
| 3,953,599 | 4/1976 | Kilmer et al. | 514/947 |
| 4,309,414 | 1/1982 | Inagi et al. | 424/81 |
| 4,507,287 | 3/1985 | Dixon | 514/43 |
| 4,540,572 | 9/1985 | Seth | 424/81 |
| 4,543,251 | 9/1985 | Kamishita | 514/161 |
| 4,545,992 | 10/1985 | Kamishita | 514/161 |
| 4,710,497 | 12/1987 | Hella et al. | 514/947 |

FOREIGN PATENT DOCUMENTS 162560 of 1983 Japan .

*Primary Examiner*—Stanley J. Friedman
*Attorney, Agent, or Firm*—Bryan, Cave McPheeters & McRoberts

[57] ABSTRACT

A percutaneous absorption preparation which comprises calcium salt of an acidic anti-inflammatory or analgesic drug having carboxyl group as the active ingredient and present in an amount of 0.3–10% by weight; a medium for the active ingredient which is selected form the group consisting of an ethylene glycol mono-lower alkyl ether, propylene glycol, polyethylene glycol and dimethylsulfoxide, the medium being present in an amount at least sufficient to dissolve the active ingredient; an absorption promotor selected from the group consisting of 1-dodecylazacycloheptan-2-one, hexamethylenelauramide, N-methyl-2-pyrrolidone, a sucrose aliphatic acid ester, dimethylsulfoxide and a nonionic surfactant and present in an amount of 0.5–10% by weight; and the remaining being other reagents and/or carriers required for a desired form of the preparation.

10 Claims, 2 Drawing Sheets

PERCUTANEOUS ABSORPTION PREPARATION

BACKGROUND OF THE INVENTION

1. Field of the Invention

This invention relates to a percutaneous absorption preparation. More particularly, it relates to a percutaneous absorption preparation which comprises a calcium salt of an acidic anti-inflammatory or analgesic drug having a carboxyl group as the active ingredient.

2. Description of the Prior Art

Acidic anti-inflammatory drugs such as indomethacin, mefenamic acid, flufenamic acid or ketoprofen have been widely used orally. However, the benefit of the full therapeutic effect thereof is often limited because of gastrointestinal side effects. Accordingly, the introduction of their rectal suppositories have allowed increased utilization for therapeutic purposes, it has however, been shown that the manifestations of peptic ulceration and rectal bleeding also occur with these suppositories. A rectal suppository of calcium salts of the acidic anti-inflammatory drugs is proposed and disclosed in Japanese Unexamined Patent Publication No. 162,560/1983, which however states that the concentration in the blood upon application of the rectal suppository is nearly equal to that of the rectal suppository of the corresponding free acid type drug.

On the other hand, gel preparations for external use of the acidic anti-inflammatory drugs or sodium salts thereof are known (e.g., U.S. Pat. No. 4,545,992 and U.S. Pat. No. 4,543,251).

SUMMARY OF THE INVENTION

This invention provides a percutaneous absorption preparation which comprises a calcium salt of an acidic anti-inflammatory or analgesic drug having a carboxyl group as the active ingredient and being present in an amount of 0.3–10% by weight; a medium for the active ingredient which is selected from the group consisting of an ethylene glycol mono-lower alkyl ether, propylene glycol, polyethylene glycol and dimethylsulfoxide, the medium being present in an amount at least sufficient to dissolve the active ingredient; an absorption promoter selected from the group consisting of 1-dodecylazacycloheptan-2-one, hexamethylenelauramide, N-methyl-2-pyrrolidone, a sucrose aliphatic acid ester, dimethylsulfoxide and a nonionic surfactant, present in an amount of 0.5–10% by weight; and other reagents and/or carriers required for a desired form of the preparation.

When the preparation of to the invention is percutaneously applied, it can maintain a therapeutically effective concentration in the blood of the active ingredient and exert systemic effect thereof, e.g., over 24 hours after application once a day, with less irritating action to the skin.

DESCRIPTION OF THE PREFERRED EMBODIMENT

Figure 1:
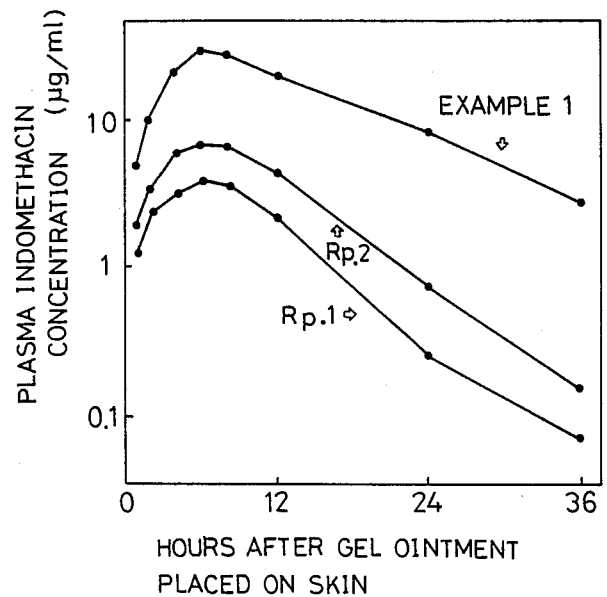
FIG. 1 is a graph illustrating the plasma concentrations of indomethacin after application of the gel ointment of Example 1, the control ointment and the comparable ointment to rat abdominal skin.

The percutaneous absorption preparation of the invention may be in the form of a gel ointment, gel cream, solution or aerosol, or in other known forms which can be pharmaceutically and topically used.

Examples of the calcium salt of acidic anti-inflammatory or analgesic drug having carboxyl group as the active ingredient include the calcium salts of ibufenac, alclofenac, metiazinic acid, suxibuzone, oxepinac, sulindac, fentiazic, indomethacin, diclofenac, bendazac, mefenamic acid, flufenamic acid, zomepirac, tolmetin, fenbufen, ibuprofen, ketoprofen, oxaprozin, flurbiprofen, naproxen, benoxaprofen, pranoprofen, suprofen, fenoprofen, CN-100 [2-(10,11-dihydro-10-oxodibenzo[b,f]thiepin-2-yl)propionic acid], Y-9213 [2-{4-[2-imidazo-(1,2-a)-pyridyl]phenyl}propionic acid], tiaprofenic acid or protizinic acid. The preferred active ingredients are the calcium salts of indomethacin, diclofenac, bendazac, mefenamic acid, ketoprofen or alclofenac.

The calcium salts of acidic anti-inflammatory or analgesic drugs can be prepared, for example, by treating the corresponding sodium salt with calcium acetate in an aqueous medium.

The amount of the active ingredient in the preparation is in the range of 0.3–10% by weight, preferably 0.4–5%, more preferably 0.5–2.0%.

The medium for the active ingredient is an diethylene glycol mono-lower alkyl ether such as diethylene glycol monoethyl ether, propylene glycol, polyethylene glycol or dimethylsulfoxide, or mixtures thereof. The preferred medium is diethylene glycol monoethyl ether or dimethylsulfoxide. It is found that the use of such medium is essential in order to dissolve the active ingredient and obtain the desired effects of the invention. For example, when a conventional ointment base is used for the calcium salt as the active ingredient, it will result in an ointment with very poor absorption of the active ingredient. The medium is used in an amount at least sufficient to dissolve the active ingredient, depending upon the particular medium and active ingredient utilized.

It is also found that the use of specific absorption promoters is effective for the preparation of the invention. For example, the addition of calcium thioglycolate which is known as an absorption promoter will dramatically decrease the absorption of the active ingredient as indomethacin calcium. Thus, the preferred absorption promoters are 1-dodecylazacycloheptan-2-one (available as Azone ® of Nelson Research and Development), hexamethylenelauramide, sucrose aliphatic acid ester (e.g., sucrose laurate or sucrose palmitate), N-methyl-2-pyrrolidone, dimethylsulfoxide and/or a nonionic surfactant (e.g., polyethylene glycol oleoyl ester, polyethylene glycol lauryl ether or sorbitan monostearate). The more preferred examples are 1-dodecylazacycloheptan-2-one, hexamethylenelauramide, N-methyl-2-pyrrolidone and sucrose laurate (or palmitate). The most preferred absorption promotor is 1-dodecylazacycloheptan-2-one or hexamethylenelauramide. The absorption promoters may be used in admixture and usually are used in an amount of 0.5–10% by weight of the preparation.

When the preparation is in a gel ointment or gel cream, other reagents and carriers required therefor are used. The reagents comprise a gelatinizing agent, an absorption adjuvant, and optionally, a neutralizing agent.

Examples of the gelatinizing agents include carboxyvinyl polymers such as Carbopol® 934, 940 or 941 (available from Goodrich Chemical Co., USA) and Hiviswako® 103, 104, 105 or 106 (available from Wako Junyaku Kogyo KK., Japan), cellulose derivatives such as hydroxyethyl cellulose, carboxymethyl cellulose or methyl cellulose; or propylene glycol alginate. The preferred gelatinizing agents are the carboxyvinyl polymers. The gelatinizing agent is usually used in an amount of 0.5-2% by weight in the final preparation and also generally used in a dilute solution in water, glycols such as propylene glycol or butylene glycol or a lower alkanol such as ethanol, or mixture thereof. Such solvents for the gelatinizing agent are also deemed to be carriers of the preparation when carboxyvinyl polymers are employed. The resulting preparation will be acidic and therefore it is preferred to neutralize it to a pH of about 6.0–7.5 by addition of the neutralizing agent in order to avoid a possible decomposition of the calcium salt as the active ingredient. Examples of the neutralizing agent include an organic amine such as diisopropanolamine, and an inorganic base such as aqueous ammonia. In any case, the use of the neutralizing agent, which does not cause any side effect on the skin, is desirable.

It is found that the use of the absorption adjuvant in a gel ointment or gel cream is effective. Examples of the absorption adjuvants include $C_{1-5}$ alcohol esters of $C_{4-14}$ aliphatic monocarboxylic acids or $C_{1-3}$ alcohol diesters of $C_{4-10}$ aliphatic dicarboxylic acids, such as ethyl caproate, diisopropyl adipate or diethyl sebacate. The absorption adjuvant is preferred to be in an amount of 0.5–5% by weight in the final preparation.

Gel ointment or gel cream may contain conventional carriers such as lanolin, vaselin or the hydrophilic ointment (Japanese Pharmacopeia).

When the preparation is in solution form, lower alcohols such as ethanol are preferably used as a carrier. When used in the form of an aerosol fluorohydrocarbons such as trichlorofluoromethane (available as Freon 11 of du Pont) or dichlorodifluoromethane (available as Freon 12 of du Pont), or liquefied petroleum gas may be used as propellant.

In addition, the preparation of this invention may be included in an adhesive tape.

The percutaneous preparation of the present invention exerts remarkable anti-inflammatory and analgesic activities after percutaneous application, due to the excellent absorption of drugs, the active ingredients as shown in the following examples. The preparations thus make to facilitate decreased gastro-intestinal irritation and ulceration and the percutaneous administration anti-inflammatory drugs in patients requiring parenteral therapy.

Accordingly, in accordance with one aspect of the invention, a method is provided for treating a patient suffering rheumatoid arthritis, osteoarthritis, acute musculo-skeletal disorders, contusion, sprain or the like which comprises percutaneously applying the above mentionedpreparation to the patient. The amount to be applied depends upon the condition or disease, age, the kind of the preparation or the like. In case of a gel ointment containing 2% of the active ingredient, generally 0.14 g or less of the gel ointment is applied per 1 cm square of skin, whereby a similar effect to oral administration will be achieved.

The following examples are given to illustrate the present invention but are not intended to limit the invention in any manner.

EXAMPLE 1

Gel ointment 1

The gel ointment is compounded from the following ingredients:

| | |
|---|---|
| Calcium salt of indomethacin | 21 g |
| Hiviswako ® 104 (Wako Junyaku Co., Ltd.) | 10 g |
| Dimethylsulfoxide | 100 g |
| Ethanol | 300 g |
| Diisopropanolamine | 11 g |
| Diisopropyl adipate | 20 g |
| Sorbitan monooleate | 50 g |
| Azone ® (Nelson Research and Development) | 50 g |
| Purified water q.s. to | 1000 g |

METHOD OF PREPARATION

Sorbitan monooleate is added with Azone (A). Hiviswako 104 is swollen with 200 g of water (B). (A) and (B) are mixed and stirred sufficiently to mix homogeneously (C). Calcium salt of indomethacin is dissolved with dimethylsulfoxide (D). (D) is added to (C) and mixed, and followed by addition of ethanol and diisopropyl adipate (E). Both diisopropanolamine dissolved in 100 g of water and the remaining water are added to (E) and homogeneously mixed.

EXAMPLE 2

Gel ointment 2

| | |
|---|---|
| Calcium mefenamate | 22 g |
| Carbopol ® 940 (Goodrich Chemical Group) | 10 g |
| Hydroxyethyl cellulose | 10 g |
| Diethylene glycol monoethyl ether | 100 g |
| Ethanol | 300 g |
| Diisopropanolamine | 11 g |
| N—methyl-2-pyrrolidone | 50 g |
| Purified water q.s. to | 1000 g |

METHOD OF PREPARATION

Carbopol 940 and hydroxyethyl cellulose are swollen with 300 g of water (A). Calcium mefenamate is dissolved in diethylene glycol monoethyl ether (B). N-Methyl-2-pyrrolidone is dissolved in ethanol (C). Diisopropanolamine is dissolved in 100 g of water (D). (A) is added to (B) and mixed homogeneously. (C) and (D) are added to the mixture and then the remaining water is added and mixed homogeneously.

EXAMPLE 3

Gel ointment 3

| | |
|---|---|
| Ketoprofen Ca | 5 g |
| Hiviswako 104 | 10 g |
| Polyethylene glycol 400 (Japanese Pharmacopea) | 100 g |
| Ethanol | 300 g |
| Diisopropanolamine | 11 g |
| Diisopropyl adipate | 20 g |
| Sucrose palmitate | 20 g |

-continued

| | |
|---|---|
| Purified water q.s. to | 1000 g |

METHOD OF PREPARATION

Sucrose palmitate is dissolved in 200 g of hot water (A). Hiviswako 104 is swollen with 200 g of water (B). (A) is added to (B) followed by mixing (C). Ketoprofen Ca is dissolved in polyethylene glycol 400 (D). (D) is added to (C) and sufficiently mixed, to which ethanol and diisopropyl adipate are added and mixed (E). Diisopropanolamine is dissolved in 100 g of water, to which (E) and the remaining water are added and well stirred.

EXAMPLE 4

Solution

| | |
|---|---|
| Indomethacin Ca | 21 g |
| Diethylene glycol monoethylether | 200 g |
| Azone | 50 g |
| Ethanol | 729 g |

EXAMPLE 5

Aerosol

| | |
|---|---|
| Alclofenac Ca | 10 g |
| Polyethylene glycol | 50 g |
| Azone | 50 g |
| Freon 11 (du Pont) | 470 g |
| Freon 12 (du Pont) | 470 g |

EXAMPLE 6

Plasma Concentrations of Anti-inflammatory Drugs After Percutaneous Application

Male Wistar rats weighing 250–300 g were divided at random into three groups, each containing 5 rats. On the day before the experiment, the hair of the abdominal area of the rats was carefully removed with an electric clipper and an electric razor to prevent damage to the stratum corneum. A 0.5 g of the gel ointment described in Example 1 was uniformly spread over the shaved abdominal skin (3×1.2 cm area) and immediately occluded with a sheet of aluminum foil and adhesive tape. The ointment remained in contact with the skin for 8 hours, and then the unabsorbed ointment was wiped off with absorbent cotton soaked in warm water. Blood samples were collected periodically for 48 hours after dosing through polyethylene tubing cannulated to the rat jugular vein, and indomethacin in plasma was determined by the gas chromatography method. The control gel ointment (Rp. 1) (Hiviswako 104 ® 10 g, indomethacin 20 g, propylene glycol 120 g, ethanol 300 g, diisopropanolamine 11 g, diisopropyl adipate 20 g and purified water q.s. to 1000 g) as a standard preparation and the comparable ointment (Rp. 2) (the preparation excluded Azone ® and sorbitan monooleate from Example 1) were applied in the same way. The results of the examination are shown in FIG. 1. The percutaneous preparation (Example 1) of the present invention gave much higher plasma levels of indomethacin over a 48-hour period than those after the control (Rp. 1) and comparable (Rp. 2) ointments.

EXAMPLE 7

The Area Under The Plasma Drug Concentration-time Curve (AUC) After Percutaneous Application of Gel Ointments The drug concentrations in plasma after percutaneous application of the calcium salts of various drugs (2%, w/w equivalent) in the form of gel ointment as described in Example 1 were measured by the procedure shown in Example 6, and compared with that of indomethacin ointment (standard preparation, Rp. 1). In Table 1, the results obtained are shown. The calcium salts of the anti-inflammatory drugs in the ointment were absorbed to a much greater degree than the indomethacin (Rp. 1). Therefore, the AUC's after topical application of these ointments were significantly greater than that after application of the indomethacin ointment (Rp. 1).

TABLE 1

| Drug | AUC (0–36 hours, μg/ml hours.) | Bioavailability (%) |
|---|---|---|
| Indomethacin | 50.4 ± 7.8 | 7.3 ± 1.4 |
| Indomethacin calcium | 473.4 ± 16.5 | 70.3 ± 4.1 |
| Diclofenac calcium | 465.3 ± 32.4 | — |
| Bendazac calcium | 460.2 ± 31.5 | — |
| Mefenamate calcium | 470.2 ± 40.5 | — |
| Flufenamate calcium | 463.3 ± 18.9 | — |

EXAMPLE 8

Figure 2:
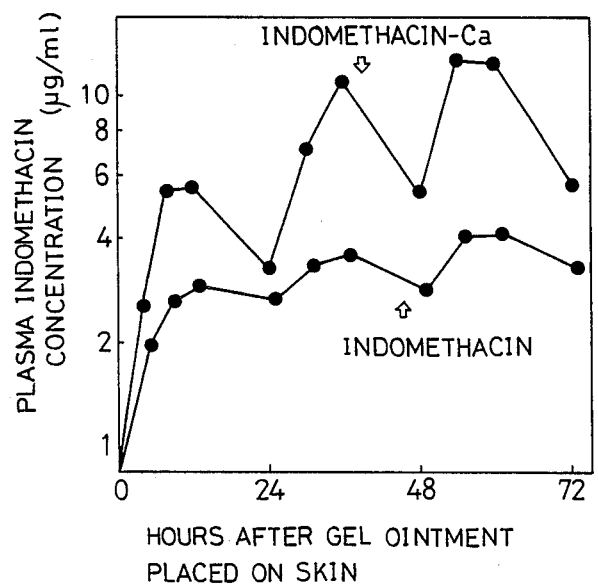
FIG. 2 is a graph illustrating the plasma concentrations of indomethacin during multiple dosing of the gel ointment of Example 1 and indomethacin ointment to rat abdominal skin.

Plasma Concentration of Indomethacin during Multiple Percutaneous Dosing of Ointment to Rats The hair of the abdominal area of male Wistar rats weighing 250–300 g was removed in the same manner as described in Example 6. 0.14 g each of the ointment described in Example 1 and indomethacin ointment (indomethacin 2.0 g was used instead of the calcium salt of the drug in the gel ointment of Example 1) were uniformly spread over the shaved abdominal skin (1.0×1.0 cm area) and immediately occluded with a sheet of aluminum foil and adhesive tape. The rats were fixed in the Bollman cages for 24 hours. The ointment remained in contact with the skin for 24 hours, and then the unabsorbed ointment was wiped off. Subsequently, second and third applications of the ointment (0.14 g, 1.0×1.0 cm area) were made at different positions on the abdomen similar to the first application. The drug concentrations were determined by the same procedure as described in Example 6. FIG. 2 depicts the plasma indomethacin concentrations after the topical application of these ointments. The results demonstrated that the calcium salt of indomethacin was readily and quickly absorbed through the skin compared with indomethacin, and that much higher plasma levels were obtained after application of the gel ointment of the calcium salt of the drug.

EXAMPLE 9

Figure 3:
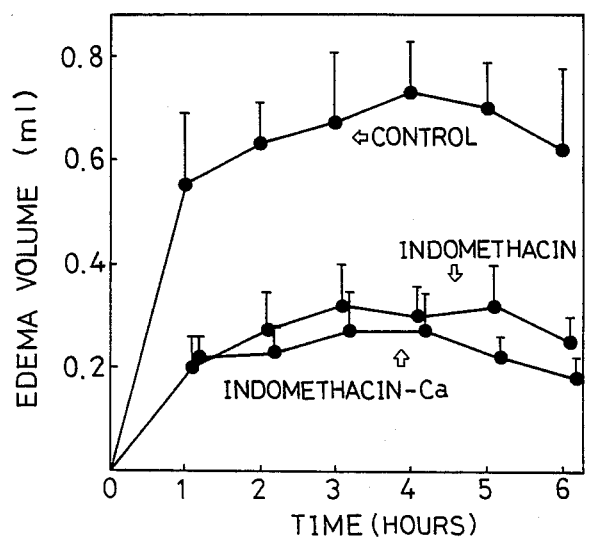
FIG. 3 is a graph illustrating the effect on carrageenan-induced paw edema of the gel ointment of Example 1 and indomethacin ointment applied to rat abdominal skin.

The Anti-inflammatory Effect of Drug Ointment on the Carrageenan-induced Edema in Hindpaw of Rat Experimental carrageenan edema was induced in groups of six male Wistar rats weighing 150–160 g. The gel ointments (0.14 g each) of the calcium salt of indomethacin (Example 1) and indomethacin (described in Example 8) were separately applied to the shaved abdominal skin. The gel without the drug was similarly applied to the control group. The treated area was immediately covered by aluminum foil and adhesive tape. Six hours later, 1% carrageenan solution was injected subcutaneously into the sole of the right hindpaw. The volumes of both hindpaw were measured hourly using a plethysmometer and the edema volume was calculated from the difference between the injected and non-injected paws. FIG. 3 indicates the effect on the carrageenan-induced paw edema of these ointments applied topically. The calcium salt of indomethacin in ointment produced significantly higher inhibitory effect.

EXAMPLE 10

The Anti-inflammatory Effect of Drug Ointment on Adjuvant Arthritis Induced with *M. butyricum*

*M. butyricum* (Difco Lab., USA) suspended in paraffin oil was injected into the sole of right hindpaw of male Wistar rats weighing 150–160 g. Rats with established adjuvant arthritis were taken 11 days after the injection of adjuvant (6 rats in each group) and the gel ointments (0.14 g each) of the calcium salt of indomethacin (Example 1) and indomethacin (described in Example 8) were separately applied to the shaved abdominal skin (1×1 cm area) for 24 hours, every other day from day 11 to day 15 after the injection of adjuvant. The edema volumes were calculated by measuring the volumes of both hindpaws on day 16, according to the same procedure as described in Example 9. The calcium salt of indomethacin in ointment produced significant inhibitory effect, to the same extent as the indomethacin ointment, on the adjuvant arthritis as shown in Table 2.

TABLE 2

| Drug | Foot volume (ml) | Inhibition (%) |
|---|---|---|
| Control | 3.22 ± 0.19 | — |
| Indomethacin | 2.32 ± 0.16* | 55.4 ± 10.5 |
| Indomethacin calcium | 2.38 ± 0.12* | 51.0 ± 7.6 |

Each value represents the mean ± S.D. of 6 rats.
*p <0.05 as compared with the control.

EXAMPLE 11

The Primary Skin Irritation of Gel Ointment

The primary skin irritation was measured after a 24-hours application of gel ointments (1 g each) of the calcium salt of indomethacin of Example 1 and indomethacin described in Example 8 on the shaved back skin (2.5×2.5 cm area) of male rabbits weighing 1.8–2.2 Kg under the occlusion. The evaluation of skin reactions was done by the erythema and edema scores 24 and 72 hours after application. The results are shown in Table 3. These ointments produced only slight erythema, the total erythema scores being 1.5 and 2.1, indicating that the irritation produced by these ointments was nearly negligible.

TABLE 3

| The Primary Irritation of Gel Ointment | |
|---|---|
| Ointment | Total erythema score |
| Indomethacin | 2.1 ± 0.48 |

TABLE 3-continued

| The Primary Irritation of Gel Ointment | |
|---|---|
| Ointment | Total erythema score |
| Indomethacin calcium | 1.5 ± 0.35 |

The present invention provides percutaneous formulations containing the calcium salts of anti-inflammatory drugs as effective components. By the application of the percutaneous formulations, therapeutic concentrations of the drug are maintained over prolonged time, thus facilitating decreased frequency of administration and side effects such as gastro-intestinal troubles. It is possible from the present invention to obtain a systemic effect of the anti-inflammatory drug by percutaneous application. Additionally, the preparation can be used for topical therapy. These formulations are thus very useful phamacologically.

I claim:

1. A percutaneous absorption preparation which comprises:
   (a) an active ingredient comprising a calcium salt of indomethacin or tolmetin in an amount of 0.3–10% by weight of the preparation:
   (b) a medium for the active ingredient selected from the group consisting of an ethylene glycol mono-lower alkyl ether, propylene glycol, polyethylene glycol and dimethylsulfoxide, in an amount at least sufficient to dissolve the active ingredient; and
   (c) an absorption promoter selected from the group consisting of 1-dodecylazacycloheptan-2-one hexamethylenelauramide, N-methyl-2-pyrrolidone, a sucrose aliphatic acid ester, dimethylsulfoxide and a nonionic surfactant, in an amount of 0.5–10% by weight of the preparation.

2. The preparation of claim 1, in the form of a gel ointment or gel cream containing:
   (d) a gelatinizing agent selected from the group consisting of a carboxyvinyl polymer, a cellulose ether or propylene glycol alginate, in an amount of 0.5–2.5% by weight of the preparation; and
   (e) an absorption adjuvant selected from the group consisting of diisopropyl adipate, diethyl sebacate or ethyl caproate, in an amount of 0.5–5% by weight of the preparation.

3. The preparation of claim 1, in which the gelatinizing agent is a carboxyvinyl polymer and is present in an amount of 0.5–5% by weight of the preparation.

4. The preparation of claim 1, further incorporating a neutralizing agent selected from the group consisting of organic amines and inorganic bases, in an amount sufficient to adjust the pH of the preparation to pH 6.0–7.5.

5. The preparation of claim 1, in which the absorption promoter is 1-dodecylazacycloheptan-2-one or hexamethylenelauramide.

6. The preparation of claim 1, which is in the form of a solution, and which contains ethanol as a carrier.

7. The preparation of claim 1, which is in the form of an aerosol.

8. The preparation of claim 1, in which the active ingredient is present in an amount of 0.5–2% by weight.

9. A preparation of claim 1 in which the active ingredient is the calcium salt of indomethacin.

10. A preparation of claim 1 in which the active ingredient is the calcium salt of tolmetin.

* * * * *